(12) United States Patent
Boykin, Jr.

(10) Patent No.: US 6,344,181 B2
(45) Date of Patent: Feb. 5, 2002

(54) PREDICTION OF DIABETES IMPAIRED WOUND HEALING BY URINARY NITRATE ASSAY

(76) Inventor: Joseph Boykin, Jr., 12600 Nightingale Dr., Chester, VA (US) 23831

( * ) Notice: Subject to any disclaimer, the term of this patent is extended or adjusted under 35 U.S.C. 154(b) by 0 days.

(21) Appl. No.: 09/885,410

(22) Filed: Jun. 21, 2001

Related U.S. Application Data

(62) Division of application No. 09/516,584, filed on Mar. 1, 2000.
(60) Provisional application No. 60/125,284, filed on Mar. 19, 1999.

(51) Int. Cl.[7] .......................... A61K 49/00; C12Q 1/00
(52) U.S. Cl. ......................... 424/9.2; 424/9.1; 435/4; 514/866
(58) Field of Search ..................... 424/6.1, 9.2; 435/4; 514/866

(56) References Cited

U.S. PATENT DOCUMENTS 5,912,114 A    6/1999    Hutchinson et al.

OTHER PUBLICATIONS

Schaffer, et al. "Nitric Oxide Is Decreased In Diabetic Wound Healing"; English Abstract; Langenbecks Arch Chir Suppl Kongressbd 1997; 114():519–21.
Schaffer, et al. "Nitric Oxide Regulates Wound Healing"; Journal of Surgical Research, 63, 237–240 (1996),Article No. 0254, pp. 237–240.
Veves et al. "Endothelial Dysfunction and the Expression of Endothelial Nitric oxide Synthetase in Diabetic Neuropathy, Vascular Disease, and Foot Ulceration"; Diabetes, vol. 47, pp. 457–463Mar. 1998.
Williams et al. "Impaired Nitric Oxide–Mediated Vasodilation in Patients With Non–Insulin–Dependent Diabetes Mellitus"; JACC, vol. 27, No. 3, Mar. 1, 1996, pp. 567–574.
Ulland et al. "Altered Wound Arginine Metabolism by Corticosterone and Retinoic Acid", Journal of Surgical Research 70, pp. 84–88 (1997), Article No. JR975099.
Schaffer et al. "Nitric Oxide Metabolism In Wounds", Journal of Surgical Research, 71 (1997), Article No. JR975137, pp. 25–31.
Dodson et al. "3–Nitrotyrosine Predicts Healing in Chronic Diabetic Foot Wounds Treated With Hyperbaric Oxygen", Wounds: A Compendium of Clinical Research and Practice, vol. 11, No. 6 Nov./Dec. 1999, pp. 129–135.
Baylis et al.—Measurement of Nitrite and Nitrate Levels in Plasma and Urine—What Does This Measure Tell Us About the Activity of the Endogenous Nitric Oxide System?, Circulation and Hemodynamics, Editorial Review; 1998, pp. 59–62.
Schaffer et al. "Diabetes–Impaired Healing and Reduced Wound Nitric Oxide Synthesis: A Possible Pathophysiologic Correlation", Surgery, vol. 121, No. 5, May 1997, pp. 513–519.
Catalano, et al. "Basal Nitric Oxide Production Is Not Reduced In Patients With Noninsulin–Dependent Diabetes Mellitus", Vascular Medicine, 1997, 2, pp. 302–305.
Bulgrin et al. "Nitric Oxide Synthesis is Suppressed in Steroid–Impaired and Diabetic Wounds"; Wounds: A Compendium of Clinical Research and Practice, vol. 7, No. 2, Mar./Apr. 1995, pp. 48–57.
Huszka et al. "The Association of Reduced Endothelium Derived Relaxing Factor—No Production With Endothelial Damage and Increased In Vivo Platelet Activation in Patients With Diabetes Mellitus" Thrombosis Research, vol. 86, No. 2, 1997, pp. 173–180.
Jeffrey P Bulgrin., et al.: "Arginine–free diet suppresses nitric oxide production in wounds", Journal of Nutritional Biochemistry, vol. 4, 1993, pp. 588–593.
Thomas P. Misko, et al.: "A fluorometric assay for the measurement of nitrite in biological samples", Analytical Biochemistry, vol. 214, 1993, pp. 11–16.
Mary B. Gillam, et al.: "A spectrophotometric assay for nitrate using NADPH oxidation by Aspergillus nitrate reductase", Analytical Biochemistry, vol. 212, 1993, pp. 359–365.
E. B. Jude, et al.: "The role of nitric oxxide synthase isoforms and arginase in the pathogenesis of diabetic foot ulcers: Possible modulatory effects by transforming growth factor beta 1", Diabetologia, vol. 42, Jun. 1999 (1999–06), pp. 748–757.

*Primary Examiner*—Kevin E. Weddington
(74) *Attorney, Agent, or Firm*—Banner & Witcoff, Ltd.

(57) ABSTRACT

Wound healing is impaired in many diabetics, who suffer increased risk of chronic foot ulceration and amputation. Diabetic patients with poor healing ability were found to possess significantly lower fasting urinary nitrate levels than diabetic patients with normal healing ability or non-diabetic controls, implicating decreased endogenous nitric oxide activity as the mediator of diabetes-impaired wound healing. Methods and kits are provided for predicting the wound healing ability of diabetic patients based on the levels of nitric oxide related products such as nitrate or nitrite in urine or other specimens. Methods are also provided for treating non-wound healing diabetics and monitoring diabetic ulcer treatment.

9 Claims, 2 Drawing Sheets

PREDICTION OF DIABETES IMPAIRED WOUND HEALING BY URINARY NITRATE ASSAY

This application is a divisional of Ser. No. 09/516,584, filed Mar. 1, 2000. It claims the benefit of U.S. Provisional Application No. 60/125,284, filed Mar. 19, 1999, which is hereby incorporated by reference in its entirety.

TECHNICAL FIELD OF THE INVENTION

The invention is related to the area of wound healing in diabetes. In particular it is related to assays for the level of nitric oxide in non-healing diabetics.

BACKGROUND OF THE INVENTION

Diabetes affects an estimated 15 million people in the United States. Within the diabetic population are individuals with chronic, non-healing lower extremity ulceration (LEU), which is associated with significant morbidity and treatment costs. Chronic, non-healing LEU precedes about 85 % of the lower extremity amputations (LEA) that over 50,000 diabetics experience annually (G E Reiber, E J Boyko, D G Smith, in Diabetes in America, NIH Publication No. 95-1468, Bethesda, Md., ed. 2, 1995, pp. 409–428). This represents more than half of all individuals receiving LEA in this country. While only 6% of diabetic hospitalizations are associated with LEU, the total government reimbursement for diabetic lower extremity complications in 1992 exceeded $1.5 billion, not including costs for limb amputation and rehabilitation. Clinical pathophysiologic risk factors for LEA include diabetic neuropathy, lower extremity ischemia, and chronic, non-healing diabetic foot ulcers.

The underlying problem in diabetics with LEU is impaired wound healing, which is poorly understood. While the majority of diabetics exhibit "normal" wound healing, those presenting with chronic LEU often demonstrate decreased wound inflammation, recurrent wound infections, decreased cutaneous vascular perfusion, poor wound collagen deposition, and scar maturation. Platelet derived growth factor (PDGF) deficiency is associated with the chronic diabetic ulcer and contributes to impaired healing (H D Beer, M T Longaker, S Werner, J Invest Dermatol 109, 132 (1997)). Clinical trials using Regranex® have shown efficacy in improving chronic foot ulcer healing in only half or less of the patients evaluated (D L Steed, J Vasc Surg, 21, 71 (1995)).

Recent research on the role of nitric oxide (NO) in wound inflammation, tissue repair, and microvascular homeostasis has allowed us to consider NO as a primary regulator of wound healing (D Bruch-Gerharz, T Ruzicka, V Kolb-Bachofen. J Invest Dermatol. 110, 1 (1998); M R Schaffer et al., Surgery 121, 513 (1997)). A systemic deficiency of endothelial-derived NO has been observed in all diabetics (A Veves et al., Diabetes, 47, 457 (1998); M Huszka et al., Thrombosis Res, 86(2), 173 (1997); S B Williams, J A Cusco, M A Roddy, M T Hohnston, M A Creager, J. Am. Col. Cardiol., 27(3), 567 (1996)), suggesting that NO plays a fundamental role in the pathogenesis of chronic, non-healing LEU. Consequently, there is a need to correlate NO production with wound healing ability in diabetics. Such a correlation would allow the development of methods to predict the wound healing ability of diabetics based on their production of NO and would provide a useful clinical indicator which could serve as a basis for choosing appropriate therapy.

SUMMARY OF THE INVENTION

It is an object of the invention to provide a method of determining whether a diabetic subject is a wound healing diabetic or a non-wound healing diabetic. The method comprises the steps of: (a) collecting a specimen from the subject; (b) determining the level of a nitric oxide related product in the specimen; and (c) comparing the level of the nitric oxide related product in the specimen with a threshold value which discriminates between wound healing and non-wound healing diabetics. If the level of the nitric oxide related product is above the threshold value, then the subject is a wound healing diabetic. If the level of the nitric oxide related product is approximately at or below the threshold value, then the subject is a non-wound healing diabetic.

It is also an object of the invention to provide a method of treating a diabetic subject. The method comprises the steps of: (a) collecting a specimen from the subject; (b) determining the level of a nitric oxide related product in the specimen; and (c) comparing the level of the nitric oxide related product in the specimen with a threshold value which discriminates between wound healing and non-wound healing diabetics; and (d) treating the subject according to whether the subject is a wound healing diabetic or a non-wound healing diabetic.

It is a further object of the invention to provide a method of monitoring the effectiveness of treatment of a non-wound healing diabetic patient. The method comprises the steps of: (a) administering to the patient a therapeutic agent designed to raise the level of nitric oxide in the patient; (b) collecting a specimen from the subject; and (c) determining the level of a nitric oxide related product in the specimen as a measure of the effectiveness of the treatment.

It is yet another object of the invention to provide a kit for determining whether a diabetic subject is a wound healing diabetic or a non-wound healing diabetic. The kit comprises reagents for determining the level of a nitric oxide related product in a specimen and instructions for obtaining the specimen, using the reagents, and interpreting the results.

These and other objects of the invention are provided by one or more of the embodiments described below.

DETAILED DESCRIPTION OF THE INVENTION

Figure 1:
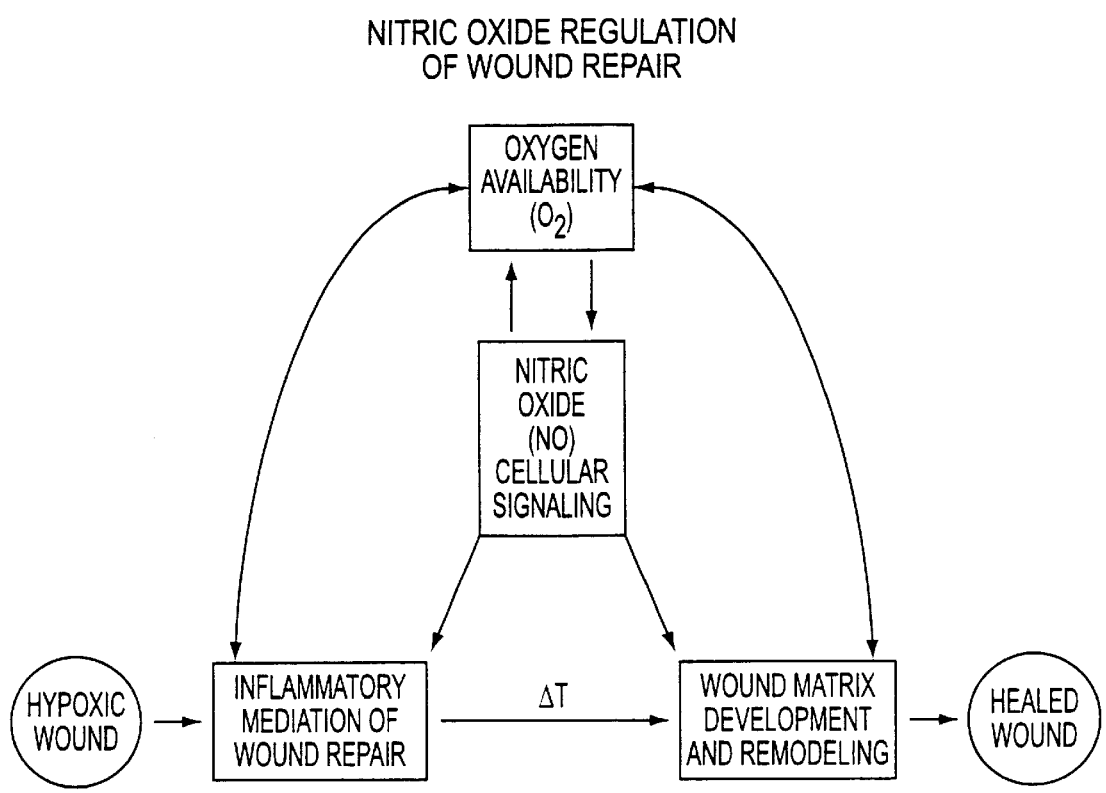
FIG. 1 presents a schematic representation of the role of nitric oxide (NO) in wound repair regulation. Wound NO mediated "cellular signaling" appears to enhance the inflammatory mediation of repair, wound oxygen availability, and wound matrix remodeling and maturation.

The methods and kits of the invention are designed to detect, treat, and monitor diabetic patients with poor wound healing ability based on measurement of the breakdown products of NO in specimens taken from the patient under controlled conditions. The invention presumes that diabetic patients represent a continuous spectrum of NO synthetic capability and that diabetics at the lower end of that spectrum have impaired wound healing function. NO is normally metabolized to the stable products nitrate and nitrite, which may be assayed in urine, plasma, tissue, or other specimens from diabetic patients. The level of nitrate or nitrite in a specimen can serve as an indicator of the level of NO synthesis in a patient. The findings of the inventor indicate that below a threshold level of NO in the diabetic patient, normal wound repair is not achieved, resulting in LEU.

NO is a small, hydrophobic gaseous free radical which is an important physiological mediator for autonomic functions such as vasodilatation, neurotransmission, and intestinal peristalsis. NO provides cellular signaling by activation of its target molecule, guanylate cyclase, which elevates intracellular concentrations of cyclic guanosine monophosphate (cGMP) (J S Beckman, in Nitric Oxide, J. Lancaster, Jr., Ed. (Academic Press, N.Y.), chap. 1). Cellular signaling is performed without mediation of channels or cellular membrane receptors and is dependent upon the concentration of NO in the cellular environment.

NO has a half-life of about five seconds in biological tissues. It is generated by three isoforms of nitric oxide synthase (NOS), which metabolize L-arginine and molecular oxygen to citrulline and NO. Two of the three isoforms are constitutive enzyme systems (cNOS) which are described in neuronal cells (nNOS) and in endothelial cells (eNOS) (D Bruch-Gerharz, T Ruzicka, V Kolb-Bachofen. J Invest Dermatol. 110, 1 (1998)). With these isoforms, increased levels of intracellular calcium activate the enzymes via calmodulin. The calcium-dependent cNOS systems produce low (picomolar) concentrations of NO. The third system is the inducible isoform (iNOS) which is calcium independent. The expression of iNOS is induced by tissue-specific stimuli such as inflammatory cytokines or bacterial lipopolysaccharide (LPS). The inducible isoform releases NO in much higher (nanomolar) concentrations than cNOS and has potent cytotoxic effects.

Currently, it appears that the cNOS enzymes are involved in regulating and maintaining skin homeostasis (S Moncada, A Higgs, N Eng J Med 329, 2002 (1993)). The iNOS enzymes appear to be mainly associated with inflammatory and immune responses that are also implicated in certain skin diseases. In human skin keratinocytes, fibroblasts and endothelial cells possess both the cNOS and iNOS isoforms. The wound macrophage and keratinocyte possess the iNOS isoform. In wound healing studies NO synthesis has been shown to occur for prolonged periods (10–14 days) after wounding and macrophages appear to be the major cellular source M R Schaffer, U Tantry, R A vanWesep, A Barbul. J Surg Res, 71, 25 (1997)). As a mediator of tissue repair, NO has been demonstrated to promote angiogenesis (A Papapetropoulos, G Garcia-Cardena, J A A Madri, W C Sissa. J Clin Invest, 100(12), 3131 (1997)) and cellular migration (Noiri et al., Am. J. Physiol. 279:C794 (1996)), increase wound collagen deposition and collagen cross-linking (M R Schaffer, U Tantry, S S Gross, H L Wasserburg, A Barbul. J Surg Res, 63, 237 (1996)), regulate microvascular homeostasis (vasodilatation) (D Bruch-Gerharz, T Ruzicka, V Kolb-Bachofen. J Invest Dermatol. 110, 1 (1998)), inhibit platelet aggregation (J S Beckman, in Nitric Oxide, J. Lancaster, Jr., Ed. (Academic Press, N.Y.), chap. 1), inhibit the formation of endothelial-leucocyte adhesions (A M Lefer, D J Lefer, Cardiovascular Res. 32, 743 (1996)), modulate endothelial proliferation and apoptosis (Y H Shen, X L Wang, D E Wilcken, FEBS Lett, 433(1–2), 125 (1998)), increase the viability of random cutaneous flaps (SC Um et al., Plast Reconstr Surg. 101 785 (1998); G F Pierce et al., Proc Natl Acad Sci USA. 86, 2229 (1989)), and enhance cellular immunomodulation and bacterial cytotoxicity (J S Beckman, in Nitric Oxide, J. Lancaster, Jr., Ed. (Academic Press, N.Y.), chap. 1).

In diabetics normal wound repair can be significantly compromised. In general, during the wound healing process, NO provides enhancement of tissue oxygen availability, the inflammatory mediation of repair mechanisms and wound matrix development and remodeling (FIG. 1). The major metabolic pathway for NO is to nitrate and nitrite, which are stable metabolites within tissue, plasma, and urine (S Moncada, A Higgs, N Eng J Med 329, 2002 (1993)). Tracer studies in humans have demonstrated that perhaps 50% of the total body nitrate/nitrite originates from the substrate for NO synthesis, L-arginine (P M Rhodes, A M Leone, P L Francis, A D Struthers, S Moncada, Biomed Biophys Res. Commun. 209, 590 (1995); L. Castillo et al., Proc Natl Acad Sci USA 90, 193 (1993). Although nitrate and nitrite are not measures of biologically active NO, plasma and urine samples obtained from subjects after a suitable period of fasting, and optionally after administration of a controlled diet (low nitrate/low arginine), allow the use of nitrate and nitrite as an index of NO activity (C Baylis, P Vallance, Curr Opin Nephrol Hypertens 7, 59 (1998)).

The invention provides a method of determining whether a diabetic subject is a wound healing diabetic or a non-wound healing diabetic. A "wound healing diabetic" refers to a diabetic subject whose wound healing capability is approximately the same as that of a non-diabetic subject. A "non-wound healing diabetic" refers to a diabetic subject whose wound healing capability is reduced from that of a non-diabetic subject and who consequently is at risk for LEU. For example, in one clinical study, non-wound healing diabetics were considered to be those patients with a history of one or more diabetic foot ulcers with incomplete healing after 20 weeks of Regranex® treatment (see Example 1). A subject according to the invention can be any human or animal with a diabetic condition such as diabetes mellitus. A human or animal with a diabetic condition is a human or animal whose regulation of plasma glucose concentration is defective, usually as a result of insufficient production of insulin or resistance to the physiological effects of insulin. For example, the subject can be a human patient who is diagnosed by a physician as having either type I or type II diabetes.

One method of determining whether a diabetic subject is a wound healing or non-wound healing diabetic comprises the steps of collecting a specimen from a diabetic subject, determining the level of nitrate or nitrite in the specimen, and comparing the level of nitrate or nitrite in the specimen with a threshold value that discriminates between wound healing and non-wound healing diabetics. In addition to nitrite and nitrate, other molecular species related to NO synthesis or breakdown (other "NO-related products") can be quantified in blood, urine, tissue, or other samples from a patient. For example, plasma levels of L-citrulline, which is a product of the reaction that produces NO, or cGMP, which is produced as a result of NO activation of guanylate cyclase, can be determined as a reflection of systemic NO synthesis in a patient. (F L Kiechle and T Malinski, Ann. Clin. Lab. Sci. 26, 501(1996)). Similarly, L-dimethylarginine, another product of NOS, can be detected by HPLC in human serum and used as a highly specific index of systemic NOS activity. (J Meyer et al., Anal. Biochem. 247, 11 (1997)). NO can also break down by reacting with superoxide anion in human plasma to produce peroxynitrite, which in turn can produce a variety of radicals such as ascorbyl radical and albumin-thinyl radical that can be detected using electron paramagnetic resonance (EPR) spectroscopy. (J Vasquez-Vivar et al., Biochem. J. 314, 869 (1996)). Another product of peroxynitrite is 3-nitrotyrosine, which can be detected in human plasma or other fluids by gas chromatography in tandem with mass spectrometry (E Schwedhelm et al., Anal. Biochem. 276, 195 (1999)), reversed-phase HPLC (H Ohshima et al., Nitric Oxide 3, 132 (1999)), or an ELISA method using anti-nitrotyrosine antibodies (J C ter Steege et al., Free Radic. Biol. Med. 25, 953 (1998)). Unlike nitrate or nitrite, most of these products are not subject to interference by dietary intake. Furthermore, the in situ detection of NO itself is possible with the aid of biosensors that quantify NO levels and changes in NO levels in response to stimuli. For example, the heme domain of soluble guanylate cyclase, a natural receptor for NO, can be labeled with a fluorescent reporter dye, and changes in fluorescence intentity can be determined through an optical fiber and calibrated to reveal NO levels at any desired location in the body, for example at or near a wound site (S L Barker et al., Anal. Chem. 71, 2071 (1999)). Given the rapid decomposition of NO in biological fluids, direct detection of NO should be performed in situ rather than some time following collection of a specimen.

The specimen can be any sample of fluid or tissue obtained from the subject in sufficient amount as to allow the determination of the level of nitrate, nitrite, or other NO-related product. For example, the specimen can be a sample of urine, blood (including plasma), or tissue. The specimen is preferably obtained from the subject after a period of fasting, in order to allow the level of nitrate, nitrite, or other NO-related products to achieve a stable baseline level. The period of fasting reduces interference from dietary and metabolic sources of nitrate or nitrite that are not related to NO breakdown. During the period of fasting, the subject's consumption of all solid and liquid food is reduced from his average consumption by at least 50%, 60%, 70%, 80%, 90%, or 100%. Preferably the subject's consumption of all solid and liquid food is reduced by at least 90%. More preferably the subject's consumption of all solid and liquid food is reduced by 100%. Most preferably, the subject does not consume any solid or liquid food during the fasting period. The subject's consumption of water generally is not restricted during the fasting period; however in some embodiments, the subject also consumes no water during the fasting period. The fasting period should be of sufficient duration as to allow a stable baseline to be achieved in whatever parameter is to be measured. A stable baseline is the condition in which the parameter measured, e.g., urinary nitrate, is generally reproducible and not subject to large fluctuations between repeated measurements or undue interference from dietary, metabolic, or other sources that are not related to NO metabolism. Preferably the period of fasting is at least 3, 4, 5, 6, 7, 8, 9, 10, 12, 16, 20, or 24 hours. More preferably the period of fasting is from 4 to 12 hours, or from 6 to 10 hours, or from 8 to 10 hours, or from 10 to 12 hours.

It is understood that any requirement for fasting will depend upon which NO-related product is being quantified, because some such products are hardly affected by diet; others may require only a brief fast. For example, plasma L-dimethylarginine (J Meyer et al., Anal. Biochem. 247, 11 (1997)) is unaffected by diet, whereas urinary nitrate/creatinine ratios are unaffected by diet if an overnight fast is performed prior to collecting the specimen (P S Grabowski et al., Arthritis Rheum. 39, 643 (1996)).

In some embodiments, the period of fasting is immediately preceded by a period during which the subject is administered a diet that is sufficiently low in sources of dietary nitrate or nitrite to achieve a stable baseline value of whichever NO metabolite will be determined in the specimen. For example, the diet can be one from which all vegetables and nitrate- or nitrite-preserved foods have been eliminated. The diet can also have a redused level of L-arginine compared to the subject's normal diet. For example, one diet provides a level of nitrate of less than 900 mg/kg body weight/day, and a level of nitrite of less than 9 mg/kg body weight/day.

The level of nitrate or nitrite in the specimen can be quantified by any method known in the art which provides adequate sensitivity and reproducibility. For example, the Griess reaction is a spectrophotometric assay for nitrate which can provide sensitive determination of nitrate and nitrite in biological fluid samples (M Marzinzig et al., Nitric Oxide 1, 177 (1997)). If the Griess reaction or another nitrite assay is performed both with and without reduction of nitrate to nitrite, then nitrate values can be obtained as the difference between the nitrite values obtained for the reduced sample and the non-reduced sample. The Griess assay can be made more sensitive if a fluorescent product is obtained, e.g., by reacting nitrite with 2,3-diaminonaphalene (T P Misko et al., Anal. Biochem. 214, 11 (1993)). Highly sensitive assays are also available which first reduce nitrite and nitrate (R S Braman and S A Hendrix, Anal. Chem. 61, 2715 (1989)) or any NO-related compound (M Sonoda et al., Anal. Biochem. 247, 417 (1997) to NO for detection with specific chemiluminesence reagents. A variety of protocols have also been described for detecting and quantifying nitrite and nitrate levels in biological fluids by ion chromatography (e.g., S A Everett et al., J. Chromatogr. 706, 437 (1995); J M Monaghan et al., J. Chromatogr. 770, 143 (1997)), high-performance liquid chromatography (e.g., M Kelm et al., Cardiovasc. Res. 41, 765 (1999)), and capillary electrophoresis (M A Friedberg et al., J. Chromatogr. 781, 491 (1997)).

The "level" of nitrate, nitrite, or other NO-related product usually refers to the concentration (in moles per liter, micromoles per liter, or other suitable units) of nitrate or nitrite in the specimen, or in the fluid portion of the specimen. However, other units of measure can also be used to express the level of nitrate or nitrite. For example, an absolute amount (in micrograms, milligrams, nanomoles, moles, or other suitable units) can be used, particularly if the amount refers back to a constant amount (e.g., grams, kilograms, milliliters, liters, or other suitable units) of the specimens under consideration. A number of commercially available kits can be used. One such kit is described in Example 2.

The specimen can be processed prior to determination of nitrate or nitrite as required by the quantification method, or in order to improve the results, or for the convenience of the investigator. For example, processing can involve centrifuging, filtering, or homogenizing the sample. If the sample is whole blood, the blood can be centrifuged to remove cells and the nitrate or nitrite assay performed on the plasma or serum fraction. If the sample is tissue, the tissue can be dispersed or homogenized by any method known in the art prior to determination of nitrate or nitrite. It may be preferable to remove cells and other debris by centrifugation or another method and to determine the nitrate or nitrite level using only the fluid portion of the sample, or the extracellular fluid fraction of the sample. The sample can also be preserved for later determination, for example by freezing of urine or plasma samples. When appropriate, additives may be introduced into the specimen to preserve or improve its characteristics for use in the nitrate or nitrite assay.

The threshold value of nitrate, nitrite, or other NO-related product can be determined by comparing diabetic subjects with normal and poor wound healing ability using the method of detection described above. For example, by comparing the urinary nitrate levels of a group of non-wound healing diabetics with a group of wound healing diabetics or normal subjects, preferably following the administration of a low nitrate diet and after a fasting period, the nitrate levels of the two groups can be compared as in Example 2. The threshold value can be selected from the data obtained. For example, the threshold can be chosen as a value slightly higher than the mean of the urinary nitrate level of the non-wound healing group; the threshold value should be chosen such that the urinary nitrate levels of at least 70%, 80%, 90%, 95%, 98%, or 99% of the non-wound healing diabetics tested would fall at or below the threshold. For human patients, the threshold value for nitrate in urine is between 15 and 50 micromolar. Preferably, the threshold value for nitrate in human urine is between 20 and 45 micromolar, or between 25 and 40 micromolar. More preferably, the threshold value for nitrate in human urine is 20, 25, 28, 30, 32, 35, 37, or 40 micromolar. For human patients, the threshold value for nitrate in plasma is between 2 and 20 micromolar. Preferably, the threshold value for nitrate in human plasma is between 3 and 17 micromolar, or between 4 and 16 micromolar. More preferably, the threshold value for nitrate in human plasma is 2, 4, 6, 8, 10, 12, 14, 16, 18, or 20 micromolar. When selecting a threshold value of nitrate, nitrite, or other NO-related product for use with a given type of specimen, for example human urine or plasma, it should be noted that the use of different assays or methods of standardization could shift the numerical ranges from those provided here.

Another embodiment of the invention is a method for treating a diabetic subject. In order to practice this embodiment, a subject is first identified as either a wound healing diabetic or a non-wound healing diabetic by the method described above, or by another method. Since non-wound healing diabetics, as identified by the invention, suffer from reduced NO activity, they can be treated by any therapy which is designed to increase NO production. Such therapies include, but are not limited to, administration of L-arginine through increasing its presence in the diet, oral administration of a dietary supplement comprising L-arginine in any pharmaceutically acceptable form, or parenteral or intravenous injection of a pharmaceutically acceptable preparation comprising L-arginine. The dosage can be selected from any protocol known in the art which is designed to increase NO production in the patient. A further therapy which increases NO production is hyperbaric oxygen therapy. Optionally, the administration of any therapy designed to increase NO production in a subject can be combined with the method described below to monitor the effectiveness of the therapy in enhancing NO levels in the subject. If the subject is found to be a wound healing diabetic, the preferred treatment does not involve a therapeutic agent designed to increase NO production in the subject. In the case of a wound healing diabetic subject, a different type of therapy can be employed. For example, administration of PDGF (Regranex®, or another PDGF preparation) can be effective to promote wound healing in a wound healing diabetic subject.

The invention can also be used to avoid therapies which may be disadvantageous for certain diabetic patients. Any negative therapeutic influence on the synthesis of nitric oxide or its effectiveness in promoting wound healing can be minimized through the use of the invention. For example, glucocorticoid drugs are sometimes administered to diabetic patients with LEU for their anti-inflammatory effect. However, glucocorticoids are known to selectively inhibit the expression of iNOS (M W Radomski, R M Palmer, S Moncada, Proc Natl Acad Sci USA 87, 10043 (1990)), and have been shown to decrease the amount of nitrite/nitrate in wound fluid (A E Ulland, J D Shearer, M D Caldwell, J Surg Res 70, 84 (1997). For patients identified as non-wound healing diabetics, whose NO synthetic capability is expected to be reduced compared with wound healing diabetics, the use of steroids that would further suppress NO levels in the patient is undesirable. Thus, according to one embodiment of the invention, a patient identified as a non-wound healing diabetic is not treated with glucocorticoids or other drugs suspected to reduce NO levels in the patient.

In a different embodiment, the invention can be used as a method of monitoring the effectiveness of treatment of a non-wound healing diabetic. In this embodiment, a patient is undergoing treatment that involves administration of a therapeutic agent designed to raise the level of nitric oxide in the patient. Examples of such therapeutic agents include the L-arginine and hyperbaric oxygen treatments described above. Following administration of the therapeutic agent, the patient is monitored for effectiveness of the treatment by the method of detecting nitrate or nitrite in a specimen from the patient, as described above. If the nitrate, nitrite, or other NO-related product level in the specimen is at or below the threshold value for determining whether the patient is a wound healing or non-wound healing diabetic, then the effectiveness of the therapeutic agent is insufficient to promote wound healing. In that case, the treatment can be subsequently adjusted, for example by increasing the dose or potency of the therapeutic agent or increasing the period of exposure to the therapeutic agent. In a related embodiment, the method of monitoring the patient is repeated, and the dose or potency of the therapeutic agent, or period of exposure to the therapeutic agent, is again increased. Preferably, in this embodiment the method of monitoring and increasing the dose of the therapeutic agent is increased until the nitrate or nitrite level in a specimen from the patient is above the threshold value. It may be desirable to then maintain the therapy at the most effective dose as long as needed until the wounds of the patient have healed.

Yet another embodiment is a kit for determining whether a diabetic subject is a wound healing diabetic or a non-wound healing diabetic. The kit comprises one or more reagents for determining the nitrate or nitrite level in a specimen from a diabetic subject. The reagent or reagents can be those required by any method known in the art for determination of nitrate or nitrite in a specimen. The kit also includes a set of instructions for using the reagents to carry out the method of determining whether a diabetic subject is a wound healing diabetic or a non-wound healing diabetic, as described above. The instruction set provides information in any suitable format (e.g., printed on paper or in electronic format on a diskette, CD-ROM, or by reference to a web site or printed publication) to allow the user to collect a suitable specimen, process the specimen, use the reagent or reagents to determine the level of nitrate, nitrite, or other NO-related product in the specimen, and interpret the results obtained, i.e., to determine whether the subject is a wound healing diabetic or a non-wound healing diabetic.

The above disclosure generally describes the present invention. A more complete understanding can be obtained by reference to the following specific examples, which are provided herein for purposes of illustration only and are not intended to limit the scope of the invention.

EXAMPLE 1

Specimen Collection from Wound Healing and Non-Wound Healing Diabetic Patients

To explore the hypothesis that non-wound healing diabetics have impaired NO activity, the following study of plasma and urinary NO metabolites—nitrate and nitrite—was carried out following a diabetic ulcer wound healing study using Regranex®. The results indicate that the chronic, non-healing LEU diabetic population is characterized by significantly decreased urinary nitrate excretion.

For the clinical study, ten (10) healthy, diabetic patients presenting with a history of one or more diabetic foot ulcers were chosen. All patients had previously received topical ulcer treatment with Regranex® gel under close clinical observation. Half of this group (n=5) experienced complete healing (healed diabetics/HD) of the ulcer by week 20 of observation. The remaining half (n=5) of this group had not experienced complete healing (unhealed diabetics/UHD) of the ulcer by week 20 of observation. Following the completion of Regranex® treatment, the 10 diabetic subjects (HD and UHD) and 10 healthy, non-diabetic controls (C) were enrolled for urine and plasma nitrate/nitrite analysis. Prior to this analysis all subjects were screened with a medical history, physical examination, and baseline hematology, serum, and urine chemistry in order to eliminate subjects with active malignant disease, rheumatic or collagen vascular disease, chronic renal insufficiency, inflammatory bowel disease, alcohol/drug abuse, cellulitis, osteomyelitis and those requiring revascularizaton surgery. For compliancy reasons, subjects determined to exhibit poor diabetic control were disqualified. Additionally, anyone receiving radiation therapy, systemic corticosteroids, and immunosuppresive or chemotherapeutic agents was disqualified. Informed consent was obtained from all study participants.

Subjects from all groups were brought into the hospital environment after having fasted for a 10-hour period. Fasting urine and plasma samples were obtained from each subject upon admission (Day-1) to provide an indication of the subject's baseline nitrate and nitrite levels. Additionally, routine labwork consisting of chemistry panel, CBC, and urinalysis was obtained from all subjects upon hospital admission. Subjects were confined to the hospital setting for 24 hours, during which time activity level, dietary intake, and other environmental factors were controlled. All subjects were restricted to bed rest with bathroom privileges and consumed the same diet during the 24hr hospitalization (2,581 Kcals; 124.2 g protein; 5,779 mg arginine; see Example 3). All subjects were required to refrain from smoking and alcohol consumption. Vegetables that usually have a higher nitrate content from fertilizers and nitrate- and nitrite-preserved foods were eliminated from the study diet, which is shown in Table 1 below. Concomitant baseline medications were administered and blood glucose monitoring was performed by the diabetic subjects per their usual home routine. Medication and dietary intake as well as urinary output were recorded and evaluated by the research team during the 24-hour confinement period. At 9 p.m. on the day of confinement, all subjects were required to begin another 10-hour fasting period. Prior to discharge from the hospital setting, the subjects again provided fasting plasma and urine samples (Day-2). Vital signs were monitored daily during confinement and all subjects were evaluated for adverse events prior to discharge. All obtained plasma and urine samples were immediately frozen at −20° C. in preparation for laboratory analysis.

TABLE 1

| Research Diet Menu | Calories | Protein (g) | Arginine (mg) |
|---|---|---|---|
| BREAKFAST | | | |
| egg, 1 | 77 | 6.3 | 377 |
| cereal, ¾ cold | 80 | 3.0 | 240 |
| toast, 1 slice, while | 61 | 2.2 | n/a |
| margarine, 1 tsp. | 45 | 0 | 1 |
| jelly, 1 tbsp. | 50 | 0 | n/a |
| orange juice, 4 oz. | 55 | 0 | 112 |
| milk, 2%, 8 oz. | 121 | 8.1 | 294 |
| LUNCH | | | |
| hamburger, 3.5 oz. | 274 | 26.6 | 1615 |
| bun | 122 | 4.4 | n/a |
| ½ sliced tomato | 15 | .5 | 8 |
| mayonnaise, 1 tbsp. | 100 | 0 | 10 |
| corn chips, 1 oz. | 153 | 1.9 | 92 |
| mixed fruit cup | 80 | 0 | n/a |
| milk, 2%, 8 oz. | 121 | 8.1 | 294 |
| DINNER | | | |
| baked chicken breast, 3.5 oz. | 222 | 29.0 | 1811 |
| rice, white, ½ c. | 133 | 4.9 | 342 |
| apples, canned, ½ c. | 68 | 0 | 6 |
| dinner roll | 85 | 2.4 | n/a |
| margarine, 1 tsp. | 45 | 0 | 1 |
| cantaloupe cubes, ½ c. | 28 | 1.4 | n/a |
| diet pudding, ½ c. | 250 | 6.2 | n/a |
| milk, 2%, 8 oz. | 121 | 8.1 | 294 |

EXAMPLE 2

Determination of Urine and Plasma Nitrate and Nitrite Concentrations in Wound Healing and Non-Wound Healing Diabetic Patients Specimens of urine and blood were obtained from the wound healing and non-wound healing diabetic subjects as described in Example 1.

Urine and plasma samples were fluorometrically assayed for nitrite and nitrate levels using a commercial kit (Cayman Chemical, Ann Arbor, Mich.) according to the manufacturer's instructions. The method used is that described by Gilliam et al. (Anal. Biochem. 212, 359 (1993)). Blood was collected in a glass tube, centrifuged, and the plasma collected and frozen until assay. The samples were thawed, vortexed and filtered with a 10 kDa size exclusion filter (Millipore, Bedford, Mass.). For the determination of nitrate, nitrate reductase and NADP was added and allowed to incubate at room temperature for two hours. Following incubation 2,3-diaminonapthalene followed by NaOH was added and the fluorscence determined with a fluorimeter using excitation at 365 nm and emission at 405 nm. Nitrite concentration was determined using the same method with the exception that nitrate reduction steps were omitted. Urine was processed in a similar fashion except that filtration was omitted. All samples were assayed in triplicate. Concentration in patient samples (micromoles per liter) was determined by comparison to standard nitrate and nitrite solutions. One-way ANOVA with Tukey-Kramer post test (Ludbrook, Clin. Exp. Pharmacol. Physiol. 18, 379 (1991)) was performed using GraphPad InStat software, version 4.10 for Windows 98. P-values <0.05 were considered significant.

Figure 2:
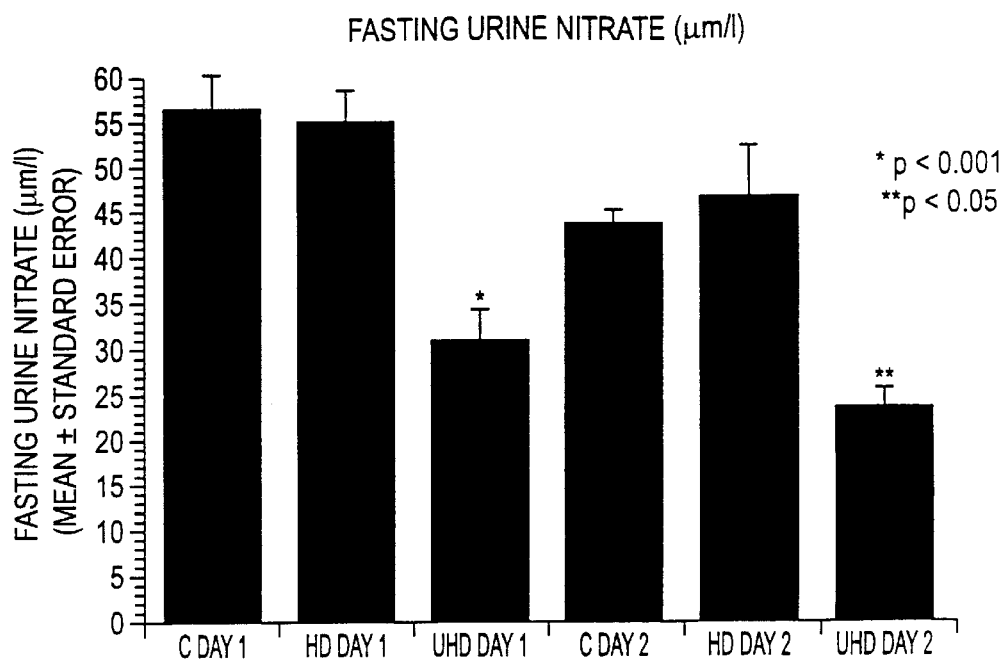
FIG. 2 is a graphical representation of the fasting urine nitrate levels (micromoles per liter) for controls (C), healed diabetics (HD), and unhealed diabetics (UHD) on days 1 and 2 of the study. Results are shown as mean±S.E., with P-values as compared to C (Pc) and HD (PHD) for each day.
Figure 3:
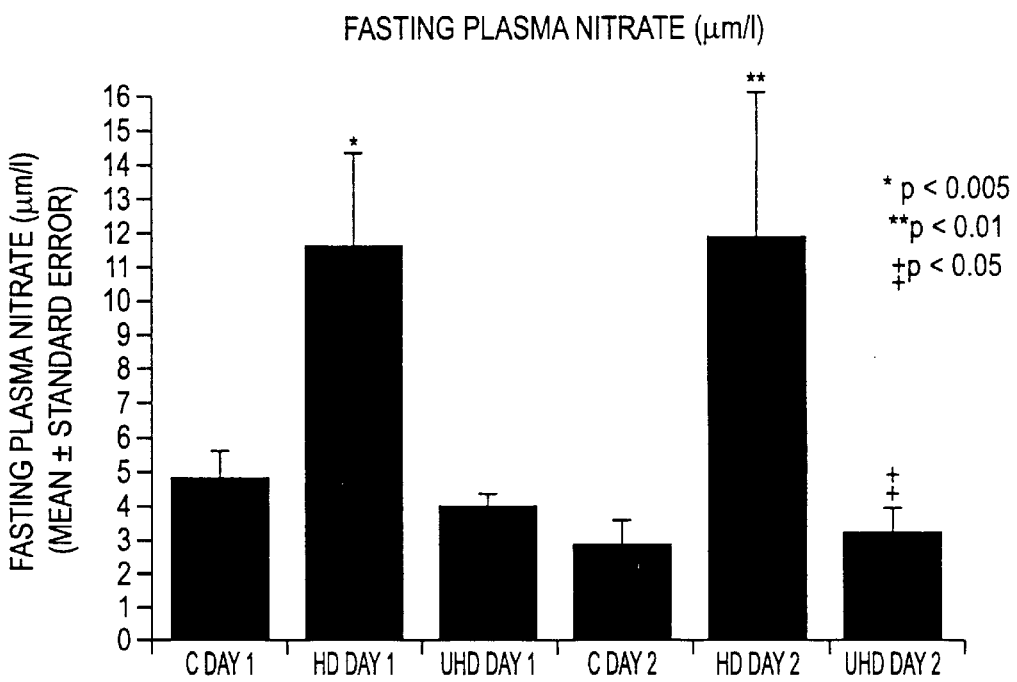
FIG. 3 is a graphical representation of the fasting plasma nitrate levels (micromoles per liter) for controls (C), healed diabetics (HD), and unhealed diabetics (UHD) on days 1 and 2 of the study. Results are shown as mean±S.E., with P-values as compared to C for each day except ‡, which compares HD and UHD for Day-2 only.

On Day-1 fasting urine nitrate levels (micromoles/l±S.E.) for groups C and HD (55.88±4.49 and 54.14±3.32, respectively) were not significantly different (FIG. 2). However, group UHD fasting urine nitrate levels (30.35±3.61) were significantly lower than groups C (p<0.001) or HD (p<0.01). Day-2 fasting urine nitrate levels for groups C and HD were lower (42.60±1.92 and 45.57±5.10, respectively) but again not significantly different. Similarly, group UHD fasting urine nitrate levels (22.74±3.13) were lower than Day-1 values and were again significantly lower than either group C (p<0.05) or HD (p<0.05) [Table 2]. Day-1 fasting plasma nitrate levels (micromoles/l±S.E.) for group C (4.80±0.85) and group UHD (4.05±0.37) were not significantly different (FIG. 3). Group HD (11.71±2.08), however, was higher than UHD, but only significantly higher than C (p<0.05). Day-2 fasting plasma nitrate levels were slightly lower for groups C (2.92±0.37) and UHD (3.16±0.61), but as before these were not significantly different. However, Group HD (11.94±4.46) was now significantly higher that either group C (p<0.01) or UHD (p<0.05). Urine and plsma nitrate levels were approximately 100 times greater than nitrite and were occasionally undetectable by this methodology. For these reasons urine and plasma nitrite levels are not reported.

TABLE 2

Fasting Urine and Plasma Nitrate Values

| | DAY 1 | | | DAY 2 | | |
|---|---|---|---|---|---|---|
| | C<br>N = 10 | HD<br>N = 5 | UHD<br>N = 5 | C<br>N = 10 | HD<br>N = 5 | UHD<br>N = 5 |
| Fasting Urine Nitrate* (μm/l) | 55.88 ± 4.49 | 54.14 ± 3.32 | 30.35 ± 3.61 | 42.60 ± 1.92 | 45.57 ± 5.10 | 22.74 ± 3.13 |
| P†, ‡ | | †NS | †.001 | | ‡NS | ‡.05 |
| Fasting Plasma Nitrate* (μm/l) | 4.80 ± 0.85 | 11.71 ± 2.08 | 4.05 ± 0.37 | 2.92 ± 0.37 | 11.94 ± 4.46 | 3.16 ± 0.61 |
| P†, ‡, § | | †0.05 | †NS | | ‡0.01 | ‡NS<br>§0.05 |

LEGEND
*Mean ± standard error
P P Value
†Compared to Controls, Day 1
‡Compared to Controls, Day 2
§Compared to HD, Day 2
C Control Group
HD Healed Diabetics
UHD Unealed Diabetics

I claim:

1. A method of monitoring the effectiveness of treatment of a non-wound healing diabetic patient, comprising the steps of:

(a) administering to the patient a therapeutic agent designed to raise the level of nitric oxide in the patient; and (b) determining the level of a nitric oxide-related product in a specimen from the patient as a measure of the effectiveness of the treatment.

2. The method of claim 1, wherein the nitric oxide-related product is nitrate, a deriviative of nitrate, nitrite, or a derivative of nitrite.

3. The method of claim 1, wherein the nitric oxide-related product is nitric oxide, L-citrulline, cGMP, peroxynitrite, 3-nitrotyrosine, or L-dimethylarginine.

4. The method of claim 1, further comprising the step of: collecting a specimen from the patient.

5. The method of claim 4, wherein the specimen is collected following a period of fasting of at least 6 hours.

6. The method of claim 1, further comprising the step of, prior to administering a therapeutic agent to the patient:

identifying the patient as a non-wound healing diabetic by comparing the level of a nitric oxide-related product in a specimen from the patient with a threshold value which discriminates between wound healing and non-wound healing diabetics, wherein if the level of the nitric oxide-related product is above the threshold value the patient is a wound healing diabetic, and if the level of the nitric oxide-related product is approximately at or below the threshold value the patient is a non-wound healing diabetic.

7. The method of claim 1, further comprising the steps of:

(c) comparing the level of the nitric oxide-related product in the specimen with a threshold value which discriminates between wound healing diabetics and non-wound healing diabetics; and (d) adjusting the treatment according to the level of the nitric oxide-related product in the specimen, wherein if the level is at or below the threshold value the administration of the therapeutic agent is increased, and if the level is above the threshold the administration of the therapeutic agent is not increased.

8. The method of claim 7, wherein if the level of the nitric oxide-related product following administration of the therapeutic agent is at or below the threshold level, the method further comprises the step of:

(e) repeating steps (a) through (d) until the level of nitric oxide-related product in a specimen from the patient is above the threshold level.

9. The method of claim 1, wherein the therapeutic agent is L-arginine or hyperbaric oxygen.

* * * * *